United States Patent [19]

Grand et al.

[11] 4,311,614
[45] Jan. 19, 1982

[54] CATALYSTS FOR WATER DEALKYLATION OF AROMATIC HYDROCARBONS

[75] Inventors: Michel Grand, Serezin du Rhone; Daniel Duprez, Poitiers, both of France

[73] Assignee: Elf Union, Paris, France

[21] Appl. No.: 154,362

[22] Filed: May 29, 1980

Related U.S. Application Data

[63] Continuation of Ser. No. 17,328, Mar. 5, 1979, abandoned.

[30] Foreign Application Priority Data

Mar. 7, 1978 [FR] France ................................ 78 06424

[51] Int. Cl.³ .................... B01J 21/04; B01J 23/42; B01J 23/44; B01J 23/46
[52] U.S. Cl. ............................ 252/466 PT; 585/487
[58] Field of Search ...................... 252/466 PT, 466 J; 585/487, 489

[56] References Cited

U.S. PATENT DOCUMENTS 2,436,923  3/1948  Haensel ........................... 252/459 X
2,922,767  1/1960  Koch ............................. 252/466 PT
3,436,434  4/1969  Lester ................................... 585/487
3,595,932  7/1971  Maslyansky et al. ................ 585/487

FOREIGN PATENT DOCUMENTS 792645  4/1958  United Kingdom ......... 252/466 PT

Primary Examiner—W. J. Shine
Attorney, Agent, or Firm—Burgess, Ryan and Wayne

[57] ABSTRACT

A water dealkylation catalyst of aromatic hydrocarbons containing at least one metal of Group VIII and eventually, one metal of group $VII_b$ deposited on a gamma alumina of special properties containing at least 1000 ppm of sulfate ions having undergone a pre-treatment in aqueous medium at a pH between 1 and 10 at a temperature below 100° C. The catalysts contain rhodium on pre-treated gamma alumina and the bimetallic catalysts contain 2 metals of the group VIII or one metal of the group VIII and one metal of the group $VII_b$ on pre-treated gamma alumina.

14 Claims, No Drawings

CATALYSTS FOR WATER DEALKYLATION OF AROMATIC HYDROCARBONS

This is a continuation of application Ser. No. 17,328, filed Mar. 5, 1979, now abandoned.

This invention relates to a water dealkylation catalyst of monoalkylated or polyalkylated aromatic hydrocarbons having improved activity, selectivity and stability.

To satisfy the demand for benzene, it is possible to dealkylate petroleum sections containing alkylated aromatic hydrocarbons. The water vapor treatment makes it possible to carry out this dealkylation by producing a gas having a high hydrogen content.

There have been proposed different processes of water dealkylation using catalysts that include metals of group VIII alone or associated with metals of other groups or with metallic oxides.

In U.S. Pat. No. 2,436,923, Haensel has first described a catalytic process of demethylation of hydrocarbons having alkyl-aromatic hydrocarbons by reaction with water or water vapor in a water/hydrocarbon molar proportion of 2/1 to 12/1 in the presence of a catalyst comprising one metal of group VIII of an atomic number higher than 27 such as cobalt, nickel, ruthenium, rhodium, palladium, osmium, iridium and platinum.

In French Pat. No. 1,588,876, Ravinovich and Maslyanskii have described a dealkylation catalyst containing one noble metal of group VIII and specially, rhodium deposited on an alumina, pure or coated with nickel or cobalt. In French Pat. No. 2,169,875, a Japanese team of the firm Mitsubishi claims the improvement of a rhodium-on-alumina catalyst by coating the base with cerium or uranium. U.S. Pat. No. 3,436,433 and 3,646,706 describe a rhodium-containing catalyst deposited on a chromium-alumina oxide coated with iron or potassium. In German Pat. No. 2,357,495, Girdler describes a water dealkylation process wherein the catalyst carrier, generally alumina, is advantageously replaced by chromium oxide. In U.S. Pat. No. 4,013,734, Exxon has recently claimed rhodium-on-alumina dealkylation catalysts improved by coating the carrier by means of vanadium. CFR describes improved performances of rhodium deposited on gamma alumina of weak activity by associating rhodium with tin in Belgian Pat. No. 844,030.

It is observed that in addition to the important part played in the dealkylation reaction by the metals of group VIII, alone or associated with other metals or metallic oxides, the carrier plays a considerable part in the behavoir of the catalyst that must have at the same time, qualities of activity noticeable by the rate of conversion, of selectivity noticeable by the degradation of the products, and lastly, of stability noticeable by the prolonged performance without regeneration.

It also appears that in the case of aluminas, the behavior of the catalyst strongly depends on physico-chemical properties and on the purity of the carrier chosen, on the one hand, and on the type of pre-treatment and the mode of deposit of the metal, on the other. For the dealkylation reaction, it is therefore clear that to describe, without specifying each one of the preceding points, a catalyst comprising one metal of group VIII deposited on gamma alumina cannot by itself constitute a sufficiently clear description of the catalytic formula.

The object of this invention is to provide improved water dealkylation catalysts of aromatic hydrocarbons containing one metal of group VIII deposited on a gamma alumina of special properties, the metal being deposited on the pre-treated alumina by an original method that confers on the catalytic system thus prepared an increased activity and selectivity associated with an excellent stability.

The dealkylation is effected within a temperature range of from 400° C. to 600° C., preferably from 430° to 550° C., at a pressure ranging from 0 to 80 bars, preferably from 1 to 60 bars.

The hourly spatial velocity of the hydrocarbons (LHSV) based on the feeding is between 0.1 and 10 h$^{-1}$, preferably between 0.3 and 4 h$^{-1}$.

The molar ratio between the water and the hydrocarbon ($H_2O$/HC) at the feeding level is from 2 to 20 and preferably, from 4 to 10.

The aluminas used in catalysis are transition aluminas of the formula $Al_2O_3 \cdot xH_2O$ with $0 < x < 1$ obtained by dehydration of the monohydrates $Al_2O_3 \cdot H_2O$ or $AlO(OH)$ (boehmite) or of the trihydrates $Al_2O_3 \cdot 3H_2O$ or $Al(OH)_3$ (gibbsite, bayerite or norstrandite). The crystallographic analysis of transition aluminas discloses numerous varieties which are more or less well crystallized. The forms most widely used as catalyst carriers are the forms eta ($\beta$) and gamma ($\gamma$) and to a lesser extent, the form chi ($\chi$). The structures of said aluminas resemble those of cubic or tetragonal spinels but possess an excess of tetracoordinated aluminum in comparison with the perfect spinel structure ($\frac{1}{3}$ tetra-coordinated aluminum ions and $\frac{2}{3}$ hexa-coordinated aluminum ions).

A detailed description of aluminas used as carriers in catalysis is given in the following works: The New Treatise of Mineral Chemistry by P. Pascal, Volume VI, pages 585 to 588 (Masson ed. 1961); Comprehensive Inorganic Chemistry by Bailar, Emeleus, Nyholm and Trotman-Dickenson, pages 1032 to 1036 (Pergamon Press), Physical and Chemical Aspects of Adsorbents and Catalysts by B. G. Linden (Academic Press 1970), and the following references; McIver, Tobin and Barth J. Catal 1963, 2,485 Stumpf, Russell, Newsome and Tucker Ind. Eng. Chem. 1950, 42, 1,398 and Leonard, Van Cauwelaert and Fripiat J. Phys. Chem. 1967, 71, 695.

It is noted that a certain ambiguity subsists in the nomenclature of the gamma aluminas. It appears in effect that the term "gamma" designates at the same time all the transition aluminas of spinel structure and a particular alumina of said series. Hereinafter, we shall give the name of "γ alumina" to an alumina corresponding to the first definition, that is, having a spinel or pseudo-spinel structure.

According to a preferred embodiment of the invention, there is used a γ alumina of large surface (γ alumina GS) having the following characteristics:

specific surface:
  50 to 350 m$^2$g$^{-1}$, preferably 150 to 350 m$^2$g$^{-1}$ total porous volume:
  0.3 to 1.3 cm$^3$g$^{-1}$, preferably 0.4 to 0.80 cm$^3$g$^{-1}$ characteristic dimension of the grains (diameter of the ball or the extruded product, for example):
  0.01 to 5 mm, preferably, 0.05 to 2 mm sulfate content:
  0.5 to 2000 ppm, preferably 0.5 to 1000 ppm residual.

Prior to introducing the active metal or metals selected, the alumina is subjected to a pre-treatment in aqueous medium at a pH between 1 and 10, preferably 3 to 9, for a period of time of from ¼ h to 78 h, preferably 1 h to 30 h, at a temperature of from 0° to 100° C., preferably 10° to 40° C.

This treatment confers on the alumina a particularly elevated power of dispersion of the metal, thus ensuring to the catalyst, a better activity and selectivity and excellent stability.

The carrier thus treated can be used moist or dry for impregnating the metal or metals, but it is preferable to use it moist quickly after the pre-treatment.

The metals are introduced by impregnation starting with an aqueous or acid solution of the salt of the chosen metal. The total concentration of metals in the carrier thus impregnated can fluctuate between 0.1 to 5%, preferably 0.1 to 2% and most preferably from 0.2 to 2% by weight.

After introduction of the specific metal or metals, the catalyst is dried and then burnt in the air. It is reduced prior to the reaction by a hydrogen current at a temperature of from 400° to 500° C.

After reduction, the catalyst is treated with a water vapor current at a temperature that can vary between 400° and 600° C. and for a period of time of from 5 min. to 15 hours, preferably from ¼ to 4 h.

The examples that follow, applied to the dealkylation of toluene, are given to illustrate the invention and without limiting it.

EXAMPLE I:

The preparation of a catalyst having 0.6% by weight rhodium deposited on a pre-treated γ alumina (catalyst No. 1).

The carrier A used is a very pure γ alumina having the following properties: specific surface: 260 $m^2g^{-1}$; porous volume 0.7 $cm^3g^{-1}$; content of sodium ion: 14 ppm; content of sulfate ion <100 ppm. The alumina appears in extruded pieces of a diameter of 1.2 mm.

120 g. of extruded pieces A are dried at 140° C. under air current and then cooled in a dessicator. They are then immersed in 275 $cm^3$ of water exchanged at room temperature and left for 5 hours while slowly stirring. The mixture is filtered, the extruded pieces are washed with 250 $cm^3$ exchanged water; they are then recovered, without drying, to immerse them in a solution of 2 g rhodium chloride hydrated in 320 $cm^3$ of 0.03 N acetic acid. The salt must be dissolved by permanent stirring for about 10 to 15 minutes at room temperature, or still better, at a temperature of from 30° to 40° C. The dark red solution must be perfectly limpid by transparence.

The extruded portions are constantly stirred for 15 minutes and then allowed to stand for 14 hours. The rhodium is then wholly adsorbed; the liquid phase has become colorless. The extruded portions are filtered, then washed three times with 100 $cm^3$ exchanged water. The catalyst is then dried at 140° C. under air for 4 hours, then burned (or calcined) in two stages: for 1 hour while progressively increasing the temperature of the atmosphere to 300° C., and then for 2 hours at 500° C. The catalyst is then cooled in a desiccator. The content in weight of the metal is 0.6%. 10 g of the catalyst thus prepared (catalyst No. 1) are placed in a dynamic reactor of fixed bed for being tested under the following conditions: temperature of the bed: 425° C.; pressure: 2 bars; V.V.h of the toluene (volume of liquid toluene passed per unit of volume of catalyst and per hour): 0.6; molar ratio $H_2O$/TOLUENE:8 at the end of 6 hours of operation, the molar yields of benzene, hydrogen, carbon monoxide, carbon dioxide and methane are respectively: 0.655; 2.10; 0.05; 0.88 and 0.35 in relation to the toluene passed; the benzene yield is then 0.88 in relation to the converted toluene. At the end of 24 hours of operation, the benzene yields are respectively 0.60 and 0.89 in relation to the toluene passed and to the converted toluene.

Note: In the foregoing, the molar yield of benzene in relation to the converted toluene represents the selectivity of benzene, and to avoid amiguity, this is referred to as "selectivity". The conversion is equal to the relation between the two benzene yields (in relation to the toluene passed, on one hand, and to the toluene converted, on the other). Thus, in the case of the preceding balance at 6 h, the rate of conversion is 0.655/0.88 that is 74%.

EXAMPLES II-III-IV-V

Different catalysts with 0.6% by weight rhodium are prepared following the method of preparation of Example I, but substituting for the exchanged water different pre-treatment solutions S.

The results are reported in Table I.

Therefore, it appears that the pre-treatment with water is preferable to pre-treatments effected with acid or basic solutions.

EXAMPLES VI, VII, VIII, IX

By way of comparison, Examples VI to IX set forth the results obtained starting with the same alumina when preparing samples of catalysts with 0.6% rhodium on alumina in accordance with the prior art.

The metal is introduced by dry or moist impregnation. The carrier is dried like in Example I but is not pre-treated.

There have been prepared 10 samples by dry impregnation. According to this method, the results are hard to reproduce even if all the necessary care is taken to standardize the preparation. In Table II there is set forth the results obtained for the most active (catalyst No. 6) and for the least active (catalyst No. 7).

5 samples have been prepared by moist impregnation. In this case, the results are quite easy to reproduce. In Table II there is set forth the results obtained for one sample (catalyst No. 8).

In Table II, there is also reported the examples given in the prior art for the catalysts: 0.6% rhodium deposited on alumina (Examples X and XI).

The preceding examples show the clear superiority of the catalysts obtained by pre-treating the alumina.

EXAMPLES XII TO XVII

The stability of the catalyst of Example I, the same as catalysts Nos. 6 and 7, have been tested for 200 h. The results are given in Table III.

The catalyst obtained by pre-treating the alumina is far more stable than the conventional catalysts.

For all catalysts, the pressure clearly increases the stability, but a much more elevated pressure is needed for a conventional catalyst to obtain the same stability as with the catalyst of Example I.

EXAMPLE XVIII 30 g of carrier used for catalyst No. 1 are dried under air current at 140° C., then cooled in the desiccator. They are then immersed in a solution of 83 mg ammonium sulfate in 20.5 $cm^3$ exchanged water. The volume of solution is calculated in a manner such that all the liquid is absorbed by the carrier. The latter is then dried at 140° C. for 2 hours, then burned (or calcined) at 500°

C. for 1 hour and cooled in the desiccator. The carrier then contains 2000 ppm of sulfate ion (in weight). It is immersed in an acetic acid solution (0.1 N) of 0.5 g rhodium chloride, the volume of which is calculated in a manner such that all the salt is absorbed. The catalyst thus prepared is dried at 140° C., then burned in accordance with the procedure set forth in Example I. The content in weight of the metal is 0.6%. 10 g of this catalyst (No. 9) are tested under the following conditions: temperature 470° C., pressure 2 bars, vvh of toluene: 0.6 molar ratio H$_2$O/TOLUENE:8. At the end of 6 h there is obtained a conversion of 18% with a selectivity of 100%.

EXAMPLES XIX AND XX

Samples having contents of added sulfate of 1000 and 500 ppm (catalysts 10 and 11) have been prepared in accordance with the procedure set forth in Example XVIII, then tested under the same conditions as catalyst No. 9.

There are respectively obtained conversions of 24 and 35% with selectivities of 100% and 95%.

EXAMPLES XXI AND XXII

There is prepared following the procedure set forth in Example VIII a catalyst with 0.6% rhodium on $\gamma$ alumina of 80 m$^2$g$^{-1}$ ($\gamma$ alumina P.S.) appearing in the form of balls of 2 to 33 mm diameter and having a sulfate content of 5000 ppm uniformly distributed in all the volume of the varrier. This catalyst (No. 12) is tested as in Example VII at 470° C. At the end of 6 hours, there is obtained a conversion of 25% with a selectivity of 94%. A carrier having the same characteristics as the one that served for catalyst No. 12 is prepared in a manner so that its residual sulfate content is only 2700 ppm.

Following the procedure of Example XXI, there is prepared a catalyst (No. 13) with 0.6% by weight rhodium that is then tested under the same conditions at 470° C.

At the end of 6 hours, there is obtained a conversion of 56% with a benzene selectivity of 86%.

The results of Examples XVII to XXII that show the influence of the sulfate ions on the behavior of rhodium catalysts deposited on alumina are set forth in Table IV.

EXAMPLES XXIII TO XXIX

The catalysts used in these examples are rhodium catalysts on alumina pre-treated with water. These catalysts are prepared using the procedure of Example I with different contents of rhodium: 0.15% (catalyst No. 14), 0.3% (catalyst No. 15); 0.6% (catalyst No. 1); 1.2% (catalyst No. 16).

These catalysts are tested under different conditions of operation; the results are set forth in Table V.

It appears that the catalysts having a low metal content are relatively not very stable; it is preferred to work with contents above 0.2%.

Comparing Examples XXV and XXVII, XXVIII and XXIX obtained with a constant VVH in relation to the active metal, it is observed that a catalyst with a considerable metal content has a behavior that is very close to other samples with a lower rhodium content. This type of catalyst is therefore most suitable for treating the charge having an elevated v.v.h., for the method of preparation described in Example I permits the dispersion of the active metal having a considerable content of alumina.

EXAMPLE XXX

A catalyst of 0.5% Rh and 0.1% Ir deposited on $\gamma$ alumina GS (catalyst No. 17) is prepared in the following manner: 30 g of carrier are pre-treated following the method set forth in Example I and then immersed in a solution containing 0.410 g hydrated rhodium chloride and 0.080 g hydrochloric acid in 80 cm$^3$ acetic acid 0.03 N. The two salts are dissolved at 40° C. for 1 hour.

The extruded portions are constantly stirred in the solution for 15 minutes, then allowed to stand for 14 hours. The metals are then totally absorbed by the carrier; the liquid phase that bathes the extruded portions is clear.

The catalyst thus prepared is washed, dried, and burned (or calcined) as in Example I. 10 g of this catalyst are tested under the same conditions as in Example I. At the end of 6 hours of operation, the benzene yield in relation to the toluene passed is 0.60; the yield is 0.91 in relation to the converted toluene. At the end of 24 h, the yields are respectively 0.56 and 0.92.

EXAMPLES XXXI TO XXXIV

Different bimetallic catalysts are prepared according to the method of Example III and then tested in a dynamic reactor under the conditions of Example I (425° C., 2 bars, v.v.h.: 0.6, molar ratio H$_2$O/TOLUENE:8).

The results are set out in Table VI.

It appears that improvements can be obtained with regard to selectivity and stability by using certain rhodium-based bimetallic associations. That is specially the case of the Rh-Ir couple in the bimetallics of the group VIII. Besides, the addition of an element of group 7b such as manganese to the rhodium catalysts on alumina is likewise a very favorable element for improving the selectivity and stability.

Bimetallic catalysts can include 2 metals of group VIII, it being possible for the relative proportions of said two metals to vary from 1/10 to 10/1. They can thus include 1 metal of group VIII, specially rhodium, and 1 metal of group VII$_b$, it being possible for the relative proportions of the metals of each group to vary from 1/10 to 10/1.

TABLE I

| EX. | Catalyst No. | S | | TEMP. | Test Conditions Pressure | V.V.H. | H$_2$O TOLUENE | Results at 6 h Conversion | Selectivity | Results at 24 h Conversion | Selectivity |
|---|---|---|---|---|---|---|---|---|---|---|---|
| II | 2 | HCL | 0.25 N | 425° C. | 2 bars | 0.6 | 8 | 67% | 82% | 60% | 84% |
| III | 3 | HCl | 0.04 N | 425° C. | 2 bars | 0.6 | 8 | 69% | 83% | 62% | 85% |
| IV | 4 | HNO$_3$ | 0.04 N | 425° C. | 2 bars | 0.6 | 8 | 64% | 89% | 58% | 89.5% |
| V | 5* | NH$_4$OH | 0.04 N | 425° C. | 2 bars | 0.6 | 8 | 70% | 83% | 64% | 85% |
| I | 1 (rap.) | water permeated | | 425° C. | 2 bars | 0.6 | 8 | 74% | 88% | 67% | 89% |

*For this catalyst pretreated in basic medium the rhodium chloride has been dissolved in exchanged water.

TABLE II

| EX. | Catalyst | Method of Impregnation | Test Conditions TEMP. | Pressure | V.V.H. | $H_2O$/TOLUENE | Results at 6 h Conversion | Selectivity | Results at 24 h Conversion | Selectivity |
|---|---|---|---|---|---|---|---|---|---|---|
| VI | 6 | dry | 425° C. | 2 bars | 0.6 | 8 | 54% | 84.5% | 46% | 84.5% |
| VII | 6 | dry | 470° C. | 2 bars | 0.6 | 8 | 82% | 72.5% | 71% | 79% |
| VIII | 7 | dry | 470° C. | 2 bars | 0.6 | 8 | 70% | 83.5% | 59% | 87% |
| IX | 8 | wet | 425° C. | 2 bars | 0.6 | 8 | 61% | 86.5% | 51% | 87% |
| X | — | — | 460° C. | 1 bar | 0.5 | 4 | 60% | 90% | | |
| XI | — | — | 470° C. | 1 bar | 1 | 4 | 48% | 89% | | |

TABLE III

Standard conditions of each test: VVH of toluene: 0.6; molar ratio $H_2O$/TOLUENE: 8.

| Example | Catalyst No. | Temp. | Pressure | 6h Conv. | Sel. | 24 h Conv. | Sel. | 50 h Conv. | Sel. | 200 h Conv. | Sel. |
|---|---|---|---|---|---|---|---|---|---|---|---|
| XII | 1 | 425° C. | 2 bars | 74% | 88% | 67% | 89% | 65% | 90% | 63% | 91% |
| XIII | 1 | 425° C. | 6 bars | 75% | 88% | 69% | 89% | 68% | 91% | 67% | 92% |
| XIV | 6 | 470° C. | 2 bars | 82% | 72.5% | 70% | 79% | 65% | 80% | 61% | 82% |
| XV | 6 | 470° C. | 6 bars | 83% | 78% | 72% | 82% | 67% | 84% | 65% | 88% |
| XVI | 6 | 470° C. | 31 bars | 77% | 78% | 75% | 80% | 74% | 81% | 73% | 83% |
| XVII | 7 | 470° C. | 2 bars | 70% | 83.5% | 59% | 87% | 52.5% | 89% | 44% | 96% |

TABLE IV

Influence of the $SO_4$ ions on the behavior of catalysts with 0.6% rhodium on γ aluminas. Test at 470° C., 2 bars, v.v.h Toluene: 0.6; molar ratio $H_2O$/HC = 8.

| Ex. | Catalyst | Alumina | Sulfate Residual content ppm | Sulfate addition ppm | after 6 hours Conversion | Selectivity |
|---|---|---|---|---|---|---|
| XVIII | 9 | GS | 100 | 2000 | 18% | 100% |
| XIX | 10 | GS | 100 | 1000 | 24% | 100% |
| XX | 11 | GS | 100 | 500 | 35% | 95% |
| VIII | 7 | GS | 100 | 0 | 70% | 83.5% |
| XXI | 12 | PS | 5000 | 0 | 24% | 94% |
| XXII | 13 | PS | 2700 | 0 | 56% | 86% |

TABLE V

| Ex | Cata | Metal Content | Temp. | Pressure | $H_2O$/HC | VVH | 6 h Conversion | Selectivity | 24 h Conversion | Selectivity |
|---|---|---|---|---|---|---|---|---|---|---|
| XXIII | 14 | 0.15% | 440° C. | 2 bars | 8 | 1.2 | 26% | 87% | 20% | 86% |
| XXIV | 15 | 0.30% | 440° C. | 2 bars | 8 | 1.2 | 43% | 88% | 37% | 87% |
| XXV | 1 | 0.60% | 440° C. | 2 bars | 8 | 1.2 | 63% | 88% | 56% | 86% |
| XXVI | 16 | 1.2% | 440° C. | 2 bars | 8 | 1.2 | 82% | 79% | 80% | 82% |
| XXVII | 14 | 0.15% | 440° C. | 2 bars | 8 | 0.3 | 64% | 90% | 50% | 89% |
| XXVIII | 15 | 0.30% | 440° C. | 2 bars | 8 | 0.6 | 66% | 89% | 54% | 88% |
| XXIX | 16 | 1.2% | 440° C. | 2 bars | 8 | 2.4 | 63% | 86% | 53% | 85% |

TABLE VI

| Example | Catalyst Number | Metals Content | | Results at 6 h Conversion | Selectivity | Results at 24 h Conversion | Selectivity |
|---|---|---|---|---|---|---|---|
| XXXI | 18 | 0.6% Rh | 1% Mn | 72% | 90% | 66% | 90.5% |
| XXXII | 19 | 0.5% Rh | 0.1% Pt | 63% | 92% | 50% | 92.5% |
| XXXIII | 20 | 0.5% Rh | 0.1% Pd | 61% | 92% | 50% | 93% |
| XXXIV | 21 | 0.5% Rh | | 63% | 89% | 56% | 90% |
| XXX | (17 rap.) | 0.5% Rh | 0.1% Ir | 66% | 91% | 60% | 92% |
| I | (1 rap.) | 0.6% Rh | | 74% | 88% | 67% | 89% |

What is claimed is:

1. A water dealkylation catalyst for an aromatic hydrocarbon consisting essentially of from 0.1 to 5% by weight of (A) one or two metals selected from the group consisting of rhodium, platinum, palladium and iridium or (B) Rh with at least one metal selected from the group consisting of Pt, Pd, Ir and Mn deposited on a gamma alumina carrier, said catalyst having improved properties of activity, selectivity and stability wherein said catalyst is prepared by:
   (a) pretreating said gamma alumina carrier in an aqueous medium for 15 minutes to 78 hours, at a pH from 1 to 10, at a temperature of 0° to 100° C.;
   (b) impregnating the pretreated gamma alumina carrier with an aqueous or acid solution of a salt of the metal, to a total concentration of metal in the carrier of from 0.1 to 5% by weight;
   (c) drying said impregnated carrier;
   (d) calcining said dried impregnated carrier in air;
   (e) reducing the calcined impregnated carrier in a hydrogen current at 400°–500° C.;
   (f) treating the reduced impregnated carrier with a water vapor current at 400° to 600° C. for a period of 5 minutes to 15 hours whereby the catalyst is formed.

2. A catalyst according to claim 1, wherein said carrier is a gamma alumina of spinel or pseudo-spinel structure of a specific surface of 50 to 350 $m^2g^{-1}$, a total porous volume of 0.3 to 1.3 $cm^3g^{-1}$, a grain diameter of from 0.01 to 5 mm, and a residual sulfate content of 0.5 to 2000 ppm.

3. A catalyst according to claim 1 or 2, wherein said carrier is pre-treated in the presence of deionized water.

4. A bimetallic catalyst according to claim 1, wherein the relative proportions of the two metals is from 1:10 to 10:1.

5. A bimetallic catalyst according to claim 4, containing 0.05% rhodium and 0.1% iridium.

6. A bimetallic catalyst according to claim 1, containing 0.6% rhodium and 1% manganese.

7. A catalyst according to claim 1 wherein the total concentration of metals in the impregnated carrier vary between 0.2 to 2% by weight.

8. A catalyst according to claim 2 wherein the carrier is a gamma alumina of spinel or pseudo-spinel structure of a specific surface of 150 to 350 $m^2g^{-1}$.

9. A catalyst according to claim 2 wherein the grain diameter of the carrier varies from 0.05 to 2 mm.

10. A catalyst according to claim 2 wherein the total porous volume of the carrier varies from 0.4 to 0.80 $cm^3g^{-1}$.

11. A catalyst according to claim 2 wherein the residual sulfate content of the carrier varies from 0.5 to 1000 ppm.

12. A catalyst according to claim 4 wherein the total concentration of metals on the impregnated carrier varies from 0.1 to 2% by weight.

13. A catalyst according to claim 1 wherein the total concentration of metals deposited on the impregnated carrier varies from 0.1 to 2% by weight.

14. The catalyst of claim 1 wherein the metal is Rh or a mixture of Rh with at least one metal selected from the group consisting of Pt, Pd, Ir and Mn.

* * * * *

UNITED STATES PATENT AND TRADEMARK OFFICE
CERTIFICATE OF CORRECTION

PATENT NO. : 4,311,614
DATED : January 19, 1982
INVENTOR(S) : Michel Grand, et al It is certified that error appears in the above—identified patent and that said Letters Patent is hereby corrected as shown below:

Column 1, line 37: "No. 2,357,495" should be

-- No. 2,357,496 --.

Column 2, line 19: "AL$_2$O$_3$.H$_2$O" should be --Al$_2$O$_3$.H$_2$O-- line 24: "eta ($\beta$)" should be --eta ($\eta$)--

Column 4, line 8 : "amiguity" should be --ambiguity--.

Signed and Sealed this

Twenty-first Day of December 1982

[SEAL]

Attest:

GERALD J. MOSSINGHOFF

Attesting Officer          Commissioner of Patents and Trademarks